Jan. 28, 1975 W. A. WARRINER Plant Pat. 3,677
ROSE PLANT
Filed Dec. 26, 1973
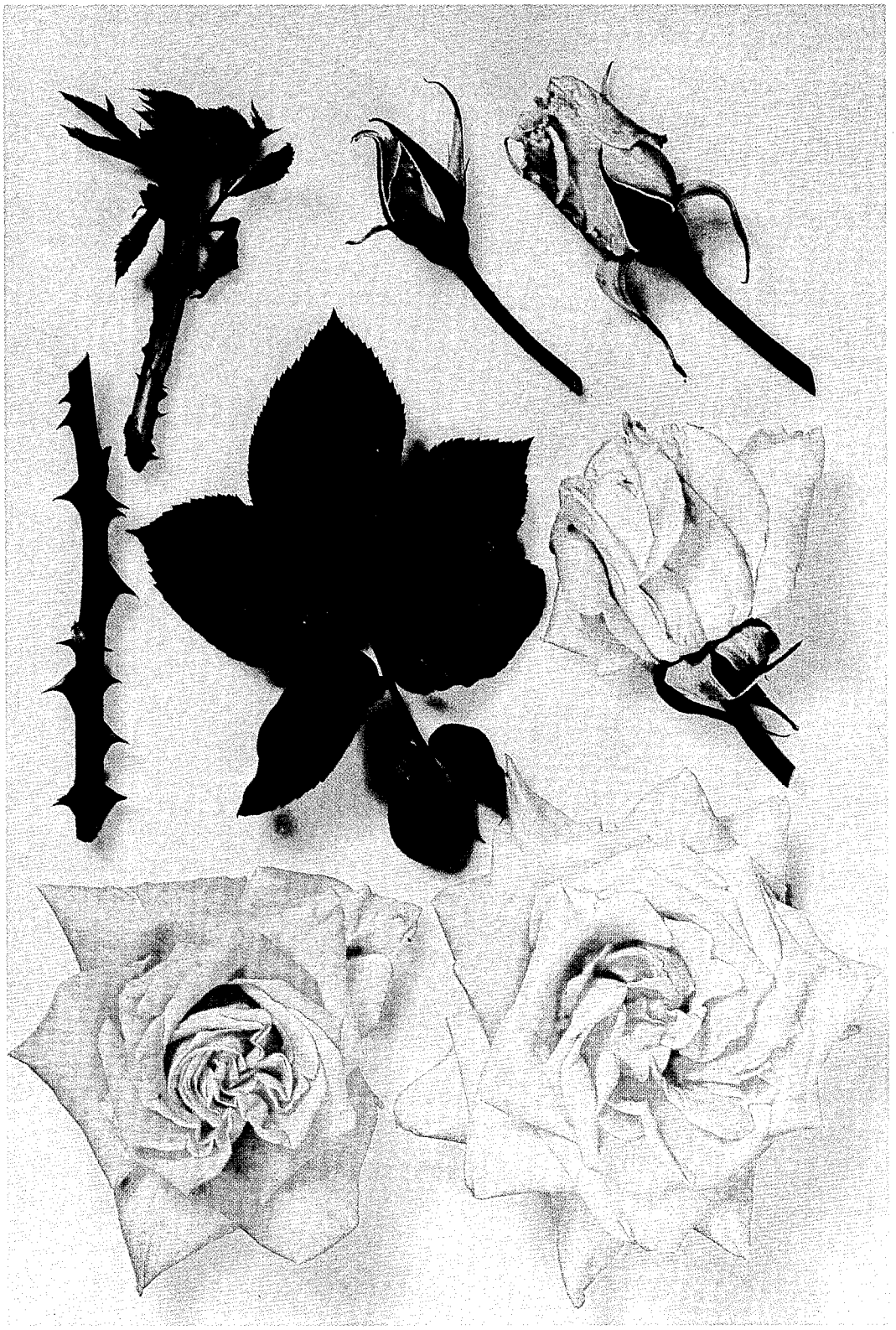

United States Patent Office

Plant Pat. 3,677
Patented Jan. 28, 1975

3,677
ROSE PLANT

William A. Warriner, Tustin, Calif., assignor to Jackson & Perkins Company, Medford, Oreg.

Filed Dec. 26, 1973, Ser. No. 427,845
Int. Cl. A01h *5/00*
U.S. Cl. Plt.—17 1 Claim

ABSTRACT OF THE DISCLOSURE

This present invention relates to a new and distinct cultivar of rose plant of the hybrid tea class which was originated by me by crossing the cultivar South Seas, U.S. Plant Pat. No. 2,184, with pollen from the cultivar Hawaii, U.S. Plant Pat. No. 1,833.

SUMMARY OF THE INVENTION

The primary objective of this breeding was to produce a new rose cultivar combining the color of the male parent, Hawaii, with plant characteristics of the female parent, South Seas. This objective was substantially achieved along with other desirable improvements as evidenced by the following unique combination of characteristics which are outstanding in my new cultivar and which distinguish it from its parents as well as from all other cultivars of which I am aware:

1. An upright plant habit, more vigorous than Hawaii.
2. Foliage that is similar to that of South Seas in shape and color of leaflets.
3. A flower color similar to but deeper than that of Hawaii but does not have the characteristic of deepening with age as do flowers of South Seas.
4. Very little fragrance.

Asexual reproduction of this new cultivar by budding as performed at Wasco, Calif., shows that the foregoing characteristics and distinctions come true to form and are established and transmitted through succeeding propagations.

BRIEF DESCRIPTION OF DRAWING

The accompanying illustration shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with *Wilson's Horticultural Color Chart*—W, and *Munsell Book of Color*—M, except where ordinary dictionary significance of color is indicated.

Parentage: Seedling.
- *Seed parent.*—Seedling of South Seas, Plant Pat. 2,184.
- *Pollen parent.*—Hawaii, Plant Pat. 1,833.

Classification:
- *Botanic.*—Rosa hybrid.
- *Commercial.*—Hybrid tea.

FLOWER

Observations were made at Irvine, Calif., in mid August 1973.

Blooming Habit: Recurrent—continuous.

Bud:
- *Size.*—1⅜ to 1½ inches when petals start to unfurl.
- *Form.*—Long, pointed.
- *Color.*—When sepals first divide—Near Red (5.0 R) value 4, chroma 12 M (5.0 R 4/12). When half blown; upper side of petals—Near Jasper Red (018 to 018/1) W gradually blending to a hue near Nasturtium Red (14/1) W near base of petal and with a pronounced Buttercup Yellow (5) W area at base of petal; lower side of petals—essentially like upper side.

- *Sepals.*—Color: Outer surface—Center area Garnet Brown (00918/3) W and along edges Scheeles Green (860/2) W. Inner surface—Scheeles Green (860/2) W with light covering of white tomentum. Three appendaged sepals lightly appendaged. Two unappendaged sepals hairy edged.
- *Receptacle.*—Color: Darker than Scheeles Green (860) W, overlaid with areas of Garnet Brown (00918/3) W. Shape: Funnel. Size: Broad. Surface: Smooth.
- *Peduncle.*—Length: Medium. Surface: Prickly. Color: Garnet Brown (00918/3) W. Strength: Stiff, erect, heavy.
- *Opening.*—Spiral type opening—outer petals with more pronounced quilling effect than center—occasionally some "double" centers while opening.

Bloom:
- *Size.*—Large. Average size when fully expanded, 4–5 inches.
- *Borne.*—Mostly singly.
- *Stems.*—Long, strong.
- *Form.*—When first open, high center. Permanence—retains its form to the end; outer petal edges slightly curled.
- *Petalage.*—Number of petals under normal conditions, 30–35.
- *Color.*—Center of flower: Upper side of petals—near Red 5.0 R 5/10 M. Reverse side of petals—same color as upper side. Outer petals: Upper side of petals—same as center petals. Reverse of petals—same. Base of petals: Small pronounced area of Buttercup Yellow (5) W. General tonality from a distance—Red 5.0 R 5/10 M.
- *Variegations.*—Only slight green to white streaks on outer 2 or 3 petals.
- *Discoloration.*—General tonality at end of first day—none. By third day—Color fades slightly to areas of Red 5.0 R 5/8 M, and lighter areas (of greater exposure) Red 5.0 R 6/10 M.
- *Fragrance.*—Very slight.

Petals:
- *Texture.*—Thick.
- *Surface.*—Inside—satiny. Reverse—satiny.
- *Shape.*—Nearly round.
- *Form.*—Tips slightly recurved; edges slightly quilled.
- *Arrangement.*—Loosely imbricated.
- *Petaloids in center.*—Few.
- *Persistence.*—Drop off cleanly.
- *Lastingness.*—On the plant—long. As cut flower—long.

Reproductive parts:
- *Stamens, anthers.*—Large, many. Color—yellow. Arrangement—regular around styles.
- *Stamens, filaments (threads).*—Long. Color—yellow.
- *Pollen.*—Lemon yellow.
- *Styles.*—Loosely separated, of even lengths. Medium.
- *Stigmas.*—Color—White.
- *Ovaries.*—All enclosed in calyx.

Fruit: (not observed.)

PLANT

Form: Bush.

Growth: Vigorous, upright.

Foliage: Number of leaflets on normal mid-stem leaves, 5 or 7.

*Size.*—Large.
*Quantity.*—Normal.
*Color.*—New foliage: Garnet Brown (00918/3) W quickly changing to a color near Spinach Green (0960/3) W. Old foliage: Near Parsley Green (00962) W.

Leaflets:
*Shape.*—Oval pointed.
*Texture.*—Upper side—leathery.
*Edge.*—Serrated.
*Serration.*—Single; small.
*Petiole (rachis).* — Color — reddish. Underside—prickles.
*Stipules.*—Long, bearded.
*Disease resistance.*—Resistant to mildew under normal growing conditions at Irvine, Calif.

Wood:
*New wood.*—Color—light green. Bark—smooth.
*Old wood.*—Color—Garnet Brown (00918/3) W. Bark—smooth.

Prickles:
*Quantity.*—On main stalks from base—ordinary. On laterals from stalk—ordinary.
*Form.*—Broad base, long, hooked downward.
*Color.*—When young—transparent to brown.
*Position.*—Irregular.

Small prickles:
*Quantity.*—On main stalks—few. On laterals—few.
*Color.*—Brown.

I claim:

1. A new and distinct cultivar of rose plant of the hybrid tea class, substantially as herein shown and described, characterized particularly as to novelty by the unique combination of its vigorous, upright habit of growth; leathery foliage; flower color deeper in intensity than its pollen parent without the aging color of flowers of its seed parent.

No references cited.

ROBERT E. BAGWILL, Primary Examiner